United States Patent [19]

Braid

[11] 4,119,548

[45] Oct. 10, 1978

[54] REACTION PRODUCT OF NICKEL THIOBIS(ALKYLPHENOLATE) AND THIOBIS(ALKYLPHENOL) AND ORGANIC COMPOSITIONS CONTAINING THE SAME

[75] Inventor: Milton Braid, Westmont, N.J.

[73] Assignee: Mobil Oil Corporation, New York, N.Y.

[21] Appl. No.: 846,308

[22] Filed: Oct. 28, 1977

[51] Int. Cl.$^2$ .................... C10M 1/54; C10M 3/48; C07F 15/02; C07F 15/04
[52] U.S. Cl. .................................. 252/42.7; 44/68; 252/75; 252/400 R; 260/439 R; 260/45.75 N
[58] Field of Search ................. 252/42.7, 400 R, 75; 260/439 R; 44/68

[56] References Cited

U.S. PATENT DOCUMENTS

| | | | |
|---|---|---|---|
| 2,703,786 | 3/1955 | Young et al. | 252/42.7 |
| 2,716,090 | 8/1955 | Hakala et al. | 252/42.7 |
| 2,971,940 | 2/1961 | Fucheman et al. | 260/45.75 |
| 2,971,941 | 2/1961 | Fucheman et al. | 260/439 R |
| 3,210,277 | 10/1965 | Swift | 252/42.7 |
| 3,636,023 | 1/1972 | Murray et al. | 260/439 R |

*Primary Examiner*—Irving Vaughn
*Attorney, Agent, or Firm*—Charles A. Huggett; Raymond W. Barclay; Howard M. Flournoy

[57] ABSTRACT

Nickel (II) thiobis(alkylphenolate) complex with thiobis(alkylphenol) forms novel complexes having improved antioxidant properties which are useful in a wide range of organic media such as lubricants and plastics. These novel complexes also provide energy quenching characteristics to such organic compositions.

17 Claims, No Drawings

REACTION PRODUCT OF NICKEL THIOBIS(ALKYLPHENOLATE) AND THIOBIS(ALKYLPHENOL) AND ORGANIC COMPOSITIONS CONTAINING THE SAME

BACKGROUND OF THE INVENTION

1. Field of the Invention

This invention relates to nickel (II) thiobis(alkylphenolates) complexed with thiobis(alkylphenols) as novel compounds and to organic compositions, normally subject to oxidative degradation such as lubricants and plastics, containing a minor amount of said nickel (II) phenolate complex sufficient to impart antioxidant, UV stabilization and energy quenching characteristics thereto.

A more particular aspect of this invention is directed to the above referred to novel complex and lubricant compositions containing same, which lubricant compositions include oils of lubricating viscosity, hydrocracked lubricating oils, hydraulic oils, mineral oils or fractions thereof, automotive oils, gear oils, transmission fluids, waxes, greases and other forms, natural or synthetic, of lubricants and distillate fuel oils. These fluids normally require the presence of stabilizing agents to inhibit oxidative degradation which may be catalyzed inter alia by ultraviolet light, the presence of metals or may occur as the result of high temperature conditions.

2. Description of the Prior Art

The production of lubricant compositions, for example, lubricating oils produced by hydrocracking provides a relatively high viscosity index oil and permits the use of base stocks that would be unsuitable for other purposes. On the other hand, however, hydrocracked lubricating oils tend toward poor stability against ultraviolet light degradation, rapidly forming suspended and/or precipitated insoluble material on exposure to ultraviolet light, such as sunlight, or other sources of actinic radiation. Compounds capable of absorbing ultraviolet light, for example, hydroxybenzophenones, and hydroxyphenyl benzotriazoles, have afforded some improvement in the light stability of hydrocracked oils. Additionally lubricants may be subjected to high temperatures which tend as mentioned heretofore to catalyze oxidative degradation.

Commercially available ultraviolet stabilizers are listed by class and function and identified as to structure in the Kirk-Othmer Encyclopedia in "Encyclopedia of Chemical Technology", Second Edition, Vol. 21, pp. 115-122. British patent specification No. 1,263,910 (1972) discloses bis(stilbene-dithiolato) nickel as an antioxidant for plastic materials. The British specification also cites superior hydroperoxide decomposition capability of this additive. U.S. Pat. No. 3,832,304 discloses the use of aromatic azo compounds for stabilizing hydrocracked oils. Additionally in the patent literature, for example, U.S. Pat. Nos. 3,149,007; 3,448,662; 3,450,636 and 3,654,329 disclose the use of nickel salts complexed with dithiophosphorous compounds as being useful in lube oils and functional fluids. Further, U.S. Pat. Nos. 2,703,786; 2,716,090 and 3,210,277 disclose the use of polyvalent metals, e.g., Ni salts of alkyl phenol sulfides as oxidation inhibitors and plasticizing agents.

None of the foregoing disclosures, however, are directed to organic compositions containing the organo-sulfur-nickel (II) complexes described in accordance with this invention. For example, U.S. Pat. No. 2,971,940 describes nickel 2,2'-thiobis-(4-t-octylphenolate), structure I

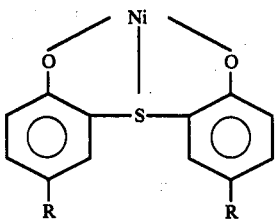

I
(NiTBP)

R = t-octyl(1,1,3,3-tetramethyl butyl)

and nickel 2,2'-thiobis-(4-t-octylphenol-phenolate), structure II

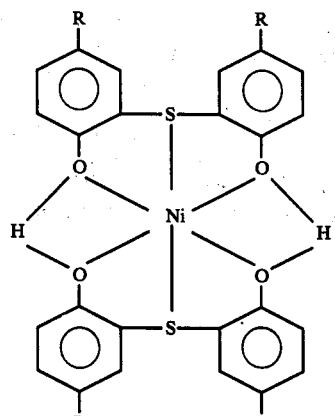

II
Ni(TBP)$_2$

R = t-octyl(1,1,3,3-tetramethyl butyl)

The subject compounds possess different properties and structures from those of I and II identified above. Although they can be prepared by methods which may involve use of the same reactants used for the preparation of I or II, the method used herein apparently distinguishes the subject complexes, exemplified by their properties, from such prior art or other previously known compounds.

SUMMARY OF THE INVENTION

This application is based on the discovery that controlled amounts of a Ni(II) thiobis(alkylphenolate) and a thiobis(alkylphenol) react in the presence of a paraffinic solvent to form a novel compound or complex having superior antioxidant characteristics to the nickel thiobis-(alkylphenol-phenolates) of the prior art, e.g., U.S. Pat. No. 2,971,940. The novel complexes of this invention also possess superior UV stabilization and energy quenching characteristics.

Therefore, this application is more particularly directed to the novel nickel compounds prepared in accordance herewith and to organic compositions thereof which comprise a major amount of an organic medium, normally susceptible to oxidative degradation, and a minor amount sufficient to impart to said organic medium antioxidant properties and ultraviolet and energy quenching stabilization characteristics.

Further the novel nickel (II) complexes embodied herein when mixed with certain arylamines and/or hindered phenols provide additional antioxidant means for the above-described organic media.

The preferred method for the preparation of the nickel complexes in accordance with the invention is to react a nickel thiobisphenolate such as structure I with a thiobis(alkylphenol) such as structure III, in a paraffinic solvent such as n-pentane, n-hexane, petroleum ether, ligroin or similar hydrocarbon solvents

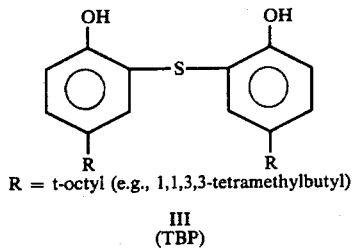

R = t-octyl (e.g., 1,1,3,3-tetramethylbutyl)

III
(TBP)

in which the thiobis(alkylphenol) is very sparingly soluble. The preferred solvents are n-pentane and n-hexane. A solution of the nickel thiobis(alkylphenolate) I is added to a slurry of the thiobisphenol (III). The reaction mixture is then stirred for a period of 2 hours to several days. The reaction mixture is usually warmed for 0.25-2 hours at a temperature of 40°-200° C. However, it is more preferred to warm the mixture at 40°-100° C. for 0.25 to 1 hour, and most preferred for 0.5 to 0.75 hour at 50°-80° C. or at the reflux temperature of the solvent.

The ratio of reactants may range from 1.1 to 2.5:1 of Compound III to Compound I. Preferred is a ratio of 1.25-2.25:1 and most preferred is a ratio 1.5-2.0:1 of Compound III to Compound I.

The complexes of this invention may be isolated in various manners, e.g., by concentrating, cooling the reaction mixture and collecting the nickel-containing solids thereby precipitated, simply heating (under the preferred conditions) a mixture of the nickel (II) thiobis(alkylphenolate) and a thiobis(alkylphenol) in the desired molar ratio and then remove the solvent. Alternatively, the complexes may be prepared in situ by heating together a mixture of reactants I and III in the desired ratio directly in the organic media to be stabilized. A further alternative method comprises the reaction of III or the sodium salt of III with a nickel carboxylate or halide as taught in U.S. Pat. No. 2,971,940 in the required ratio to produce the nickel thiobisphenolate I replacement of the reaction solvent with one of the type described above and then reaction with the desired ratio of III.

The structures of the subject complexes may be represented by one or more of the following general formulae:

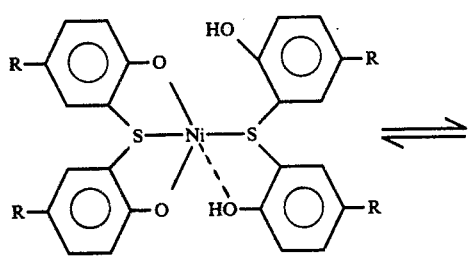

A

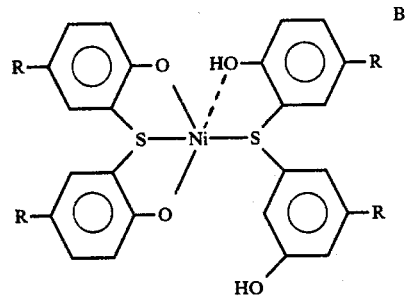

B

C

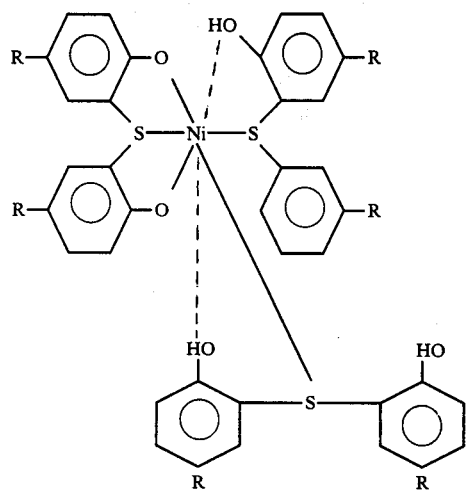

D

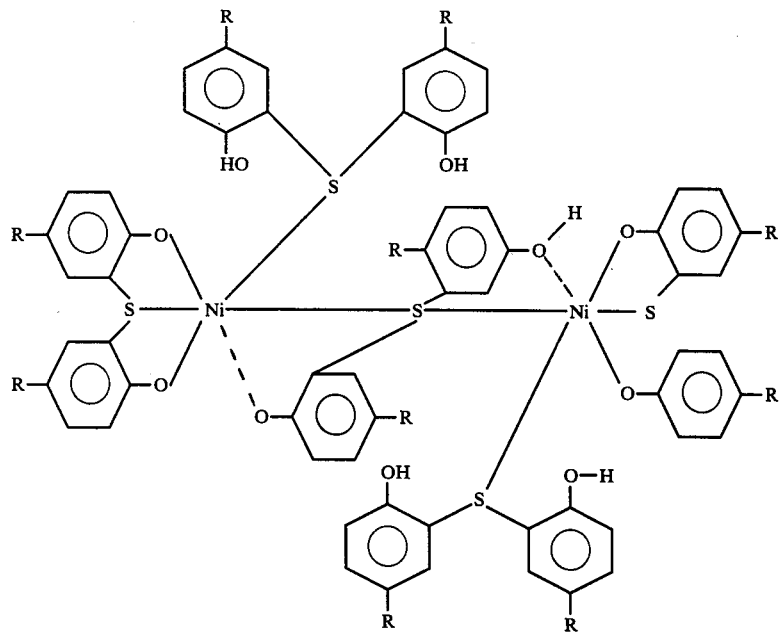

where R is H or alkyl of 1 to about 30 carbon atoms. R may also be alkyl of 4 to about 16 carbons and preferably from about 4 to 8.

The nickel thiobisphenolate compound I and the nickel thiobis(phenolphenolate) compound II are individually soluble at the concentration in paraffinic solvents at which the subject complexes precipitate. The thiobisphenol compound III has very low solubility in paraffinic solvents per se. Therefore, on cooling, excess III would be expected to precipitate from the solution free of metal whereas in the present invention the precipitate unlike III contains a significant quantity of nickel.

The melting point of the nickel thiobisphenolate I was 256°–263° C. and the melting point of thiobisphenol III was 135°–139° C., but the melting point of the complex NiTBP . (TBP)$_{1.9}$, in accordance with this invention, containing about 66 mol.% of III was 153°–158° C. Moreover, an intimate mixture of I and III in a ratio to give approximately a Ni TBP . (TBP)$_2$ complex softened at 128° C., melted at 133°–139° C. When this same mixture was heated in a small amount of n-hexane and the solvent evaporated, the solid remaining melted at 161°–164° C.; thus, clearly distinguishing the complex from the physical mixture.

A further major distinction between such structures as A, B, C. D and structure II [Ni(TBP)$_2$] is that the principal coordination in A, B, C and D involves the sulfur atoms of the thiobisphenol ligands with the nickel thiobisphenolate (structure I) element which is an integral structural element in these structures. Thus, although structure II as disclosed in the patent literature has the same overall stoichiometry as one of the complexes of the present invention made from unsubstituted 2,2'-thiobisphenol, it is clear from the elemental analysis and physical properties that this subject complex is a mixed ligand complex distinctive therefrom.

The organosulfur-containing nickel (II) complexes in accordance with the invention can be effectively employed in any amount which is sufficient for imparting to the organic medium, e.g. lubricant, the desired degree of protection against oxidative degradation. In many instances, the nickel (II) complex is effectively employed in an amount from about 0.01 to about 5%, by weight, and preferably in an amount from about 0.1 to about 2%, by weight, of the total weight of the lubricant composition. The term "Nickel (II) complex", as used herein is intended to include nickel compounds having a chelate ring formation. As hereinbefore indicated, the organic sulfur-containing nickel (II) complexes may be incorporated in any lubricating media which can include oils of lubricating viscosity and also greases in which any of the aforementioned oils are employed as vehicles. In general, synthetic oils can also be effectively protected against oxidative and UV degradation. They may also be protected in combination with mineral oils, or as grease vehicles. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis-(p-phenoxyphenyl)ether, phenoxy phenylether, etc.

The arylamines used herein are preferably selected from the group consisting of the following: N-phenyl-1-naphthylamine; N-(4'-t-octylphenyl)-1-naphthylamine; N-phenyl-2-naphthylamine; 4,4'-thiobis(N-phenyl-1-naphthylamine); 1,1'-thiobis(N-phenyl-2-naphthylamine); diphenylamine; 4,4'-di-t-octyldiphenylamine; dinaphthylamine; 4-decoxydiphenylamine; phenothiazine. Especially preferred are phenyl naphthylamines such as N-phenyl-1-naphthylamine, N-(4-t-octylphenyl)-1-naphthylamine and N-phenyl-2-naphthylamine. However, it is understood that this is a non-limiting list and any arylamine appropriate in view of those disclosed above may be used. For purposes of this application it is understood that the term arylamines is meant to include arylaminoquinones, arylaminohydroquinones and phenothiazines.

Any suitable hindered phenolic compound may be used herein. Preferred are those selected from the following non-exhaustive list: 2,6-di-t-butyl-p-cresol; 4,4'-methylenebis(2-6-di-t-butyl-m-cresol); 4,4'-butylidenebis(6-t-butyl-m-cresol) 4,4'-methylenebis-(2,6-di-t-butylphenol); 2,6-di-t-butylphenol, and 4,4'butylidinebis-(2,6-di-t-butyl-phenol); 2,4,6-tri-t-butylphenol. Especially preferred is 4,4'-methylenebis-(2,6-di-t-butylphenol).

Generally the weight ratio of nickel (II) complex to aryl amine and/or hindered phenol is from about 0.01–5.0 to 1.

DESCRIPTION OF SPECIFIC EMBODIMENTS

EXAMPLE 1

Base oil: hexadecene which simulates a typical mineral oil substrate.

EXAMPLE 2

Commercially obtained nickel II 2,2'-thiobis-(4-t-octylphenol-phenolate). It's method of preparation and structure are described in U.S. Pat. No. 2,971,940.

EXAMPLE 3

A mixture of 330 g of 2,2'-thiobis-(4-t-butyl)phenol (commercially obtained as noted in U.S. Pat. No. 3,971,940) and 247.6 g of nickel II acetate tetrahydrate in 2000 ml of xylene is heated at reflux temperature while stirring until there is no further evidence of azeotropic distillation of water or acetic acid. The xylene is removed from the extract and the residual solid is heated for 2 hours at 180°–185° C. leaving the nickel, 2,2'-thiobis-(4-t-butylphenolate) product as a tan solid.

EXAMPLE 4

To a suspension of 8.9 g of 2,2'-thiobis-(4-t-octylphenol) in 600 ml. of petroleum ether there was added a solution of 10 g. of nickel 2,2'-thiobis-(4-t-octylphenolate) in 150 ml. of petroleum ether while stirring. At room temperature the 2,2'-thiobis-(4-t-octylphenol) remained in suspension. The reaction mixture was then boiled while stirring and the thiobisphenol dissolved as the solution volume was reduced. Cooling after concentration to less than 100 ml. precipitated a green solid complex, m.p. 153°–158° C. The elemental analysis for this complex corresponded to a composition in which 1.9 molecules of the thiobisphenol are complexed with one molecule of the nickel thiobisphenolate or, overall, 2.9 molecules of the thiobisphenol are complexed with one nickel atom.

Anal. Calculated for Ni$(C_{28}H_{40}O_2S)(C_{28}H_{42}O_2S)_{1.9}$: C, 72.75; H, 9.01; S, 6.94; Ni, 4.38. Found: C, 72.76; H, 9.12; S, 6.53; Ni, 4.40.

EXAMPLE 5

A mixture of 40 g. (0.08 mole) of nickel 2,2'-thiobis-(4-t-octylphenolate) and 35.5 g (0.08 mole) of 2,2'-thiobis-(4-t-octylphenol) was heated in 500 ml. of n-hexane at reflux for 3.5 hours. The volume of the reaction mixture was then concentrated to about 250 ml. Upon cooling a fraction of the complex of two molecules of the thiobisphenol with one molecule of the nickel thiobisphenolate precipitated as a green solid m.p. 158°–161° C.

Anal. Calc'd. for Ni$(C_{28}H_{40}O_2S)(C_{28}H_{42}O_2S)_2$: C, 72.86; H, 9.03; S. 6.95; Ni, 4.24. Found: C, 73.45; H, 9.26; S. 6.72; Ni, 4.49.

EXAMPLE 6

Further concentration of filtrate of Example 5 afforded a purer fraction of this complex, a green solid, mp. 168°–171° C., for which the nickel analysis was 4.16%.

EXAMPLE 7

A mixture of 25.7 g. (0.05 mole) of nickel 2,2'-thiobis-(4-t-octylphenolate) (Example 3) and 10.9 g (0.05 mole) of 2,2'-thiobisphenol was refluxed in n-hexane for several hours. The volume of the reaction mixture was reduced to 300 ml. and the green solid which precipitated, m.p. 297°–301° C., was collected; this corresponded to a mixed 1:1 complex of nickel 2,2'-thiobis-(4-t-octylphenolate) and 2,2'-thiobisphenol.

Anal. Calc'd. for Ni$(C_{28}H_{40}O_2S)(C_{12}H_{10}O_2S)$: C, 66.94; H, 7.02; S. 8.94; Ni, 8.18. Found: C, 65.58; H, 6.61; S, 9.62; Ni, 8.55.

EXAMPLES 8 & 9

These mixtures of 2,2'-thiobis-(4-t-octylphenol) were prepared otherwise in accordance with Example 7 in very dilute hexadecane ca. 6.5% by weight. As a result, the complex formation was inefficient.

In order to evaluate the effectiveness of the organosulfur-containing nickel (II) complexes of the present invention, the following test was employed:

Oxygen Absorption Test

Oxidations were conducted in an oxygen circulation apparatus of the type described by R. W. Dornte, *Ind. Engr. Chem.*, 28, 26 (1936), modified so the rate of oxygen absorption could be recorded automatically. The 30 g. sample was placed in a 28 × 260 mm tube and allowed to equilibrate thermally before the oxygen flow was begun. Oxygen was introduced to the sample at a rate of 5 l/hr. through a fritted glass disk 3 mm from the bottom of the tube. The inhibition period, $t_{1.0}$, was taken as the time required for the absorption of 1.0 mol. oxygen per Kg of sample.

The results of the test are recorded below in Table 1.

following metals either known to catalyze organic oxidation or commonly used materials of construction.
a. 15.6 sq. in. of sand-blasted iron wire,
b. 0.78 sq. in. of polished copper wire,
c. 0.87 sq. in. of polished aluminum wire, and
d. 0.167 sq. in. of polished lead surface.

Dry air is passed through the sample at a rate of about 5 liters per hour.

One group of additives (Table 2) was tested in a solvent refined mineral oil. A second group (Table 3) was tested in the presence of a synthetic lubricant comprising a pentaerythritol ester prepared from a mixture of $C_5$–$C_9$ or $C_5$ and $C_9$ monocarboxylic acids. The first group (Table 2) was tested at 325° F. with a 40-hour air treatment and the second group (Table 3) was tested at

Table 1
Inhibition of Hexadecane Autoxidation at 175° C[1]

| Example | Additives | Conc. of Reaction Product NI(II) Complex mol./Kg | Inhibition Period for Oxygen Adsorption Hr($t_{1.0}$)[2] |
|---|---|---|---|
| 1 | None | — | 1/2/1.1 |
| 2 | Nickel (II)2,2'-thiobis-(4-t-octylphenol-phenolate) (commercial product) | 0.005 | 19.1 |
| 3 | Nickel (II)2,2'-thiobis-(4-t-octylphenol-phenolate) | 0.005 | 3.7/5.3 |
| 4 | Reaction product of equimolar Ex. 3 and 2,2'-thiobis(4-t-octylphenol) mp. 153–158° | 0.0035 | 68 |
| 5 | Ex. 4 new prep. mp. 158–161° | 0.0034 | 64.4 |
| 6 | Purer fraction from Ex. 5 mp. 168–171° | 0.0033 | 84.6 |
| 7 | Reaction product of equimolar Ex. 3 and 2,2'-thiobisphenol | 0.005 | 20.7 |
| 8 | Mixture Ex. 3 + 2,2'-thiobis-(4-t-octylphenol) | 0.0025 / 0.0025 | 8.9 |
| 9 | Mixture Ex. 3 + 2,2'-thiobis-(4-t-octylphenol) | 0.005 / 0.005 | 22.3 |

[1] Modified Dornte Test
[2] Time (hr.) required to absorb 1 mol of oxygen/Kg. of oil The complexes were further evaluated in The Catalytic Oxidation Test according to the procedure outlined below.

Catalytic Oxidation Test

A sample of the base lubricant is placed in an oven at a desired temperature. Present in the sample are the 450° F. with a 24 hour air treatment. The samples are observed for increase in acidity (NN) and kinematic viscosity (KV) after treatment, the loss in weight of the lead specimen and the relative amount of visual sludge.

Table 2
B-10A Catalytic Oxidation Test
325° F, 40 Hr., Base Stock

| Additive | Conc., Wt.% | ΔNN | ΔKV | Lead Metal Loss, mg. | Sludge |
|---|---|---|---|---|---|
| None | — | 17 | 334 | 66 | Heavy |
| Example 2 | 1 | 4.1 | 119 | 1.4 | Nil |
| Example 5 | 1 | 0.8 | 10 | 3.4 | Heavy |

Table 3
B-10X Catalytic Oxidation Test
450° F, 24 Hr., (Drew) Ester Base Stock

| Additive | Conc., Wt.% | ΔNN | ΔKV | Lead Metal Loss, mg. | Sludge |
|---|---|---|---|---|---|
| None | — | 8.3 | 586 | 13.7 | Trace |
| Example 2 | 1 | 4.98 | 119 | 1.4 | Nil |
| Example 4 | 1 | 1.7 | 42 | 2.4 | Nil |
| Example 5 | 1 | 2.6 | 247 | 3.3 | Light |
| Example 5 + N-Phenyl-1-naphthylamine | 1 / 1 | 1.6 | 114 | 3.3 | Light |
| Example 5 + 4,4'-Methylenebis-(2,6-di-t-butylphenol) | | 2.1 | 173 | 4.7 | Light |

The data tabulated in Tables 1, 2 and 3 clearly demonstrate the utility of this invention in both mineral and synthetic organic fluids. As noted from the tables, the antioxidant characteristics of the present invention, i.e., novel complexes of nickel (II) thiobisphenolates and thiobis (alkylphenols) have proven to be markedly superior in direct comparison with prior art nickel complexes.

While this invention has been described with reference to preferred compositions and components therefor, it will be understood by those skilled in the art that departure from the preferred embodiments can be effectively made and are within the scope of the specification.

What is claimed is:

1. An organosulfur-containing complex comprising a nickel (II) thiobis(alkylphenolate) with a thiobisphenol or a thiobis(alkylphenol) prepared by reacting from about 1.1 to about 2.5 moles of a thiobisphenol or a thiobis(alkylphenol) with 1 mole of a nickel thiobis(alkylphenolate) in a paraffinic solvent at temperatures of from about 40° to about 200° C.; all of said alkyl groups contain from 1 to about 30 carbon atoms.

2. The complex of claim 1 prepared by reacting from about 1.5–2.0 moles of thiobisphenol or thiobis(alkylphenol) to 1 mole of nickel thiobis(alkylphenolate) at a temperature of from about 50° to about 80° C.

3. The complex of claim 1 in which the alkyl groups contain from 4 to about 16 carbon atoms.

4. The complex of claim 3 in which the alkyl groups are $C_8H_{17}$.

5. The complex of claim 4 in which the alkyl groups are 4-t-octyl radicals.

6. The complex of claim 5 in which the alkyl groups are 1,1,3,3-tetramethylbutyl.

7. The complex prepared in accordance with claim 1 wherein the paraffinic solvent is selected from the group consisting of n-pentane, n-hexane, petroleum ether and ligroin.

8. A composition comprising a major proportion of an organic medium normally susceptible to oxidative degradation and a minor amount sufficient to impart antioxidant properties, ultraviolet stabilization and energy quenching characteristics thereto of a nickel (II) complex as described in claim 1.

9. The composition of claim 8 wherein the alkyl groups contain from 4 to about 16 carbon atoms.

10. The composition of claim 9 wherein the alkyl groups are $C_8H_{17}$.

11. The composition of claim 10 in which the alkyl groups are 1,1,3,3-tetramethylbutyl.

12. The composition of claim 8 wherein the organic medium is selected from the group consisting of oils of lubricant viscosity or greases prepared therefrom, fuel oils, hydrocracked oils, hydraulic oils, mineral oils or fractions thereof, automotive oils, gear oils, transmission fluids, or waxes.

13. The composition of claim 12 wherein the organic medium is an oil of lubricant viscosity.

14. The composition of claim 13 wherein the oil of lubricant viscosity is a mineral oil.

15. The composition of claim 13 wherein the oil of lubricant viscosity is a synthetic oil.

16. The composition of claim 15 wherein the synthetic lubricant has an ester base.

17. The composition of claim 12 wherein the lubricant composition is a grease.

* * * * *

UNITED STATES PATENT AND TRADEMARK OFFICE
CERTIFICATE OF CORRECTION

PATENT NO. : 4,119,548

DATED : October 10, 1978

INVENTOR(S) : MILTON BRAID

It is certified that error appears in the above-identified patent and that said Letters Patent are hereby corrected as shown below:

Column 5, formula, H   was omitted.

Column 7, line 65, "3,971,940" should read --2,971,940--.

Signed and Sealed this

Eighth Day of May 1979

[SEAL]

Attest:

RUTH C. MASON
Attesting Officer

DONALD W. BANNER
Commissioner of Patents and Trademarks